United States Patent [19]

Husain et al.

[11] Patent Number: 4,812,596

[45] Date of Patent: Mar. 14, 1989

[54] PROCESS FOR THE CONVERSION OF T-ALKYLPHENOL WASTE DISTILLATION BOTTOMS TO PARA-T-ALKYLPHENOL

[75] Inventors: Altaf Husain, East Norriton; Stanley R. Sandler, Springfield, both of Pa.

[73] Assignee: Pennwalt Corporation, Philadelphia, Pa.

[21] Appl. No.: 32,890

[22] Filed: Mar. 31, 1987

[51] Int. Cl.$^4$ .................. C07G 37/11; C07C 37/68
[52] U.S. Cl. ........................ 568/788; 568/756; 568/780; 568/784
[58] Field of Search ........... 568/716, 780, 784, 788, 568/756

[56] References Cited

U.S. PATENT DOCUMENTS 2,337,123  12/1943  Olin et al. ..................... 568/783
3,418,380  12/1968  Laufer et al. ................. 568/784

FOREIGN PATENT DOCUMENTS 61-200934  9/1986  Japan ........................... 568/789

OTHER PUBLICATIONS

Page 1027 of The Merck Index, Tenth Edition (1983) No. 7009.

*Primary Examiner*—Werren B. Lone
*Attorney, Agent, or Firm*—Panitch Schwarze Jacobs & Nadel

[57] ABSTRACT

A process is provided for converting waste distillation bottoms containing t-alkylphenols with substantial unknown constituents to useable para-t-alkylphenols. The process comprises heating the waste distillation bottoms with phenol and an acid catalyst to effect transalkylation. The waste distillation bottoms typically result from the production of para-t-alkylphenol and/or 2,4-di-t-alkylphenol.

17 Claims, No Drawings

PROCESS FOR THE CONVERSION OF T-ALKYLPHENOL WASTE DISTILLATION BOTTOMS TO PARA-T-ALKYLPHENOL

Background of the Invention

1. Field of the Invention

This invention relates to a process for converting waste distillation bottoms from the production of t-alkylphenols to usable para-t-alkylphenol, including the reduction of the unknown constituents in the waste distillation bottoms. The process involves heating the waste distillation bottoms with sufficient amounts of phenol and an acid catalyst to obtain the desired reduction in unknown components and to produce the desired product, thus reducing the waste which requires disposal.

By the process of the present invention, waste of a type which previously has been discarded is converted predominantly into a useful, saleable, commercial product. Para-t-alkylphenols have various uses. For example, they are used as antioxidants, bactericides, ingredients in cleaning compositions and as intermediates to make phenolic resins, coatings and ultraviolet light stabilizers. Waste products are recovered, saving the disposal cost of the waste distillation bottoms. The present invention provides an environmentally attractive process, as well, since a significant portion of the waste product, which contains a multitude of unknown impurities, does not have to be incinerated or otherwise discarded by expensive, environmentally acceptable techniques, but is converted to a useful product, para-t-alkylphenol, typically the product sought to be produced by the underlying manufacturing process which produced the waste in the first place. Thus, recovery of the primary product of the overall manufacturing process is enhanced.

2. Description of the Prior Art

U.S. Pat. No. 2,337,123 of Olin et al., issued Dec. 21, 1943, discloses that para-t-alkylphenol is produced from starting materials such as unsaturated hydrocarbons and hydroxy aromatic compounds. An intermediate isomerization process is involved in which reaction mixtures from the starting compounds including ortho-phenols and di-t-alkylphenols, such as ortho-t-amylphenol and di-t-amylphenol, are isomerized to para-t-amylphenol by being heated with acid-activated clay.

U.S. Pat. No. 3,418,380 of Laufer et al., issued Dec. 24, 1968, discloses a process involving the transbutylation of pure 2,4-di-t-butylphenol and 2,4,6-tri-t-butylphenol by heating these compounds in the presence of unsubstituted phenol and less than 0.5 percent concentrated sulfuric acid catalyst, to produce orthosubstitution of the phenol, rather than parasubstitution. This patent discloses that reaction conditions are carefully controlled to produce the desired ortho-t-butylphenol in preference to para-t-butylphenol. The patent indicates that the product will contain at least an equimolar amount of para-butyl-substituted phenol, since the butyl group in the para-position is not affected by the conditions of the reaction. It should be noted that substantially pure starting materials are used in the process of this patent and it does not relate to the use or reduction of waste distillation bottoms as in the present invention.

In contrast to the prior art, the present invention converts t-alkylphenol waste distillation bottoms containing a variety of impurities, most of which are unknown, predominantly to para-t-alkylphenol by reacting the bottoms with fresh phenol and an acid catalyst while heating. Under the conditions of this invention, the multitude of impurities associated with the waste distillation bottoms from the manufacturing process for making para-t-alkylphenol or 2,4-di-t-alkylphenol do not interfere with the process, and in most cases, are utilized in the transalkylation process of the present invention. In the process of this invention there is a substantial reduction in the waste unknowns which require disposal.

SUMMARY OF THE INVENTION

The present invention is directed to a process for reducing unknown constituents in waste distillation bottoms resulting from the production of a t-alkylphenol and for substantially simultaneously producing para-t-alkylphenol from the waste distillation bottoms comprising reacting with the waste distillation bottoms about 13 wt. % to about 50 wt. % phenol in the presence of about 3 wt. % to about 11 wt. % free acid catalyst, and maintaining an average reaction temperature of about 80° C. to about 130° C.

Further, the preferred process of this invention involves adding about 25 wt. % to about 34 wt. % unsubstituted phenol to the waste t-alkylphenol distillation bottoms from the production of para-t-alkylphenol and/or 2,4-di-t-alkylphenol followed by a sufficient amount of sulfuric acid catalyst to give a free acid content of about 3.7 wt. % to about 7 wt. % and heating to a temperature of about 110° C. to about 120° C. to produce predominantly para-t-alkylphenol along with a small amount of ortho-t-alkylphenol, 2,4-di-t-alkylphenol, and some high-boiling components.

More specifically, the present invention involves a process for using distillation bottoms which are produced as a waste from the manufacture of t-alkylphenols selected from the group consisting of para-t-alkylphenol, 2,4-di-t-alkylphenol and mixtures thereof. Preferably, the waste distillation bottoms include t-alkylphenols having t-alkyl substituents of 4 to 12 carbons, whereby the predominant para-t-alkylphenol produced by transalkylation contains 4 to 12 carbons in the alkyl substituent.

As used herein, the term "predominantly" means that the specified product is present in the greatest amount compared to the other products produced. Thus, while it is most preferred that the para-t-alkylphenol is produced as a major product, such that more than half of the product is para-t-alkylphenol, the present invention also includes the production of a predominant amount of para-t-alkylphenol, such that the para-t-alkylphenol is the greatest single identifiable product produced, even if it does not comprise more than half of the products produced. While it may not be commercially economical, the present invention also includes the production of para-t-alkylphenol in less than a predominant or major amount, since para-t-alkylphenol may be produced in a significant amount, even if other products are produced in a greater amount.

As used herein, unless otherwise indicated, the term "weight percent" or "wt. %" refers to the weight percent of a component or product represented by its characteristic curve in a gas chromatogram compared to the weight of all components or products in the sample analyzed by gas chromatography, except with respect to the phenol and acid catalyst reacting with the waste distillation bottoms. In these cases, "wt. %" of the phenol and acid is based on the weight of the waste distillation bottoms and added phenol contained in the reaction mixture.

The term "free" when used with acid catalysts, such as free sulfuric acid, refers to the amount of acid remaining after neutralizing caustic present in the waste mixture and which is thereby available for reaction.

DETAILED DESCRIPTION OF PREFERRED EMBODIMENTS

The primary purpose of the present invention is the reduction in the waste unknowns contained in waste distillation bottoms which require disposal resulting from the production of t-alkylphenols. This invention provides an environmentally attractive process for utilizing the waste by-products by converting them to saleable para-t-alkylphenol product. The waste bottoms result from the manufacture of mono-t-alkylphenols and/or di-t-alkylphenols. The particular details of the manufacturing processes which produce the waste distillation bottoms are unimportant for the purpose of carrying out or understanding the present invention. Thus, the present invention does not depend upon any particular manufacturing process to produce the waste distillation bottoms. Rather, the present invention can be used to convert to para-t-alkylphenol the waste distillation bottoms of typical processes well known to those skilled in the art for producing t-alkylphenols.

The present invention involves a process for reducing the amount of waste distillation bottoms requiring disposal and the unknown constituents therein by reacting with the waste distillation bottoms at a temperature of about 80° C. to about 130° C. and for a sufficient time, in the presence of an acid catalyst having about 3 wt. % to about 11 wt. % free acid, about 13 wt. % to about 50 wt. % of unsubstituted phenol sufficient to produce a transalkylation, whereby a significant portion of the alkylphenols from the waste distillation bottoms and the phenol are converted predominantly into para-t-alkylphenol.

It is preferred that the present invention be used to produce para-t-alkylphenols having an alkyl substituent with 4 to 12 carbon atoms, since typical commercial alkylphenols are derived from olefins having 4 to 12 carbon atoms which are reacted with phenol. Typical alkylphenols are derived from isobutylene, isoamylene, propylene trimer and propylene tetramer.

Typical waste distillation bottoms are obtained from the production by batch or continuous processes of mono-t-alkylphenol or di-t-alkylphenol, or a combination of both. A typical analysis range of the waste distillation bottoms from the preparation of para-t-amylphenol and 2,4-di-t-amylphenol, exemplary of the t-alkylphenols of the present invention, as determined by gas chromatography ("GC") techniques well known to those skilled in the art is:
phenol: none
ortho-t-amylphenol ("o-TAP"): none
para-t-amylphenol ("p-TAP"): 0–3%
2,4-di-t-amylphenol ("di-TAP"): 30–50%
unknown high boiling compounds: 40–50%
residue not subject to GC analysis: 10–20%

Exemplary of the para-t-alkylphenols produced from waste distillation bottoms in accordance with the present invention, experiments have been conducted involving the production of para-t-amylphenol, also referred to as para-t-pentylphenol. Nevertheless, the techniques and results of the process according to the present invention involving the tertiary $C_5$ alkyl substituted phenols are believed to apply to other tertiary $C_4$ through $C_{12}$ alkyl-substituted phenols, as well. For example, it is expected that the present invention would produce the desired results using waste distillation bottoms obtained from the production of t-dodecylphenols prepared using propylene tetramer, under the reaction conditions set forth in Example 1 below.

In accordance with the present invention, the waste distillation bottoms are removed from the distillation vessel and in another vessel are reacted with unsubstituted phenol and a sufficient amount of acid catalyst at an average reaction temperature of about 80° C. to about 130° C. A preferred average reaction temperature range is from about 110° C. to about 120° C., with 115° C. being presently most preferred for para-t-amylphenol. Surprisingly, the use of lower temperature, such as 63° C., gives an increase in the waste by-products (or total unknowns) which have to be disposed of. Therefore, it is important that the reaction temperature be carefully controlled in the desired range.

Reaction times vary, depending upon the type and concentration of the various components undergoing reaction, the type and amount of acid catalyst used and the temperature of the reaction, but, typically, reaction times are from about 1 hour to about 5 hours. At the preferred temperature range of about 110° C. to about 120° C., the preferred reaction time is about 2 hours to about 4 hours. The end point is determined by analysis of the resulting products, rather than by any easily observable event. Thus, the end point is determined empirically by testing, for example, by using gas chromatographic techniques performed on samples of the reaction mixture, to determine at what point the greatest amount of para-t-alkylphenol is being produced.

The para-t-alkylphenol product is recovered by adding enough NaOH to neutralize the acid, and then subjecting the reaction mixture to vacuum distillation. The particular para-t-alkylphenol produced will be distilled at its known boiling point and known pressure. For example, para-t-amylphenol can be distilled at 154.0° C. and 30mm Hg.

Although sulfuric acid is the preferred acid catalyst in this invention, and most preferably, concentrated sulfuric acid, other strong Bronsted (protonic) or Lewis acid catalysts may be used, such as hydrochloric acid, methanesulfonic acid, methanedisulfonic acid, acetonedisulfonic acid, p-toluenesulfonic acid, trifluoromethane sulfonic acid, or boron trifluoride.

To reduce the unknown components contained in the waste distillation bottoms and to obtain a predominant portion of the preferred para-t-alkylphenol from the waste distillation bottoms, the waste distillation bottoms, the phenol and the acid catalyst should be present in specified weight ratios. The acid is added to neutralize the caustic present in the distillation bottoms and to provide an amount suitable for reaction, which is termed "free" sulfuric acid. Suitable results would be obtained if the components of the reaction are present in the following weight proportions based on the weight of the waste distillation bottoms plus phenol: about 13 wt. % to about 50 wt. % phenol, and about 3 wt. % to about 11 wt. % of free acid catalyst. Most preferred amounts are about 25 wt. % to about 34 wt. % phenol, and about 5 wt. % to about 6 wt. % of the free acid catalyst. Less free acid may be used when greater amounts of phenol are used, within the indicated ranges, to obtain lowered amounts of unknowns and greater production of para-t-alkylphenols.

A preferred embodiment of the present invention is based upon the discovery that there is a unique method of adding the acid catalyst to give the optimum amount of desired para-t-alkylphenol in the transalkylation of the waste distillation bottoms. Adding the acid catalyst, such as concentrated (96%) sulfuric acid, before the addition of phenol to the waste distillation bottoms gives lower yields of the para-t-alkylphenol than when the acid catalyst is added to a mixture containing the waste distillation bottoms and the free phenol. Accordingly, to produce higher yields of the para-t-alkylphenol using the same components of the reaction, the unsubstituted phenol should be added to the waste distillation bottoms and stirred for a sufficient time to allow complete mixing of these components prior to the addition of the acid catalyst.

The present invention will now be illustrated in more detail with reference to the following specific, non-limiting examples:

EXAMPLES 1 to 14

General Procedure

A sample of dark brown-black, viscous t-amylphenol waste distillation bottoms was obtained from a commercial process for the manufacture of para-t-amylphenol and 2,4-di-t-amylphenol.

A given amount (See Table I) of the sample was placed in a round bottom, three neck flask fitted with a reflux condenser, stirrer, thermometer and drying tube in a temperature-controlled oil bath. A given amount of unsubstituted phenol was mixed with the amylphenol waste distillation bottoms in the reaction vessel. A given amount of concentrated (approximately 96%) sulfuric acid was added to this mixture. The resultant mixture was stirred, and heated at a specified average temperature for a specific time at which time a sample was taken and subjected to analysis by capillary gas chromatography. The details of Examples 1 to 14 are summarized in Table I below:

TABLE 1

Examples 1 to 14

| Exp. No. | Bottoms (g.) | Phenol (g.) | Conc. Sulfuric Acid (g.) | Basicity of Bottoms meq/g | Free conc. Sulfuric acid (1) | Average Temp. (C.) | Time (hrs.) | Initial composition (wt. %) (2) | | | | | | | |
|---|---|---|---|---|---|---|---|---|---|---|---|---|---|---|---|
| | | | | | | | | Phenol | o-TAP | p-TAP | di-TAP | High-boilers | balance | Residue | Total Unknowns | Total |
| 1 | 100.0 | 50.0 | 10.1 | 0.493 | 5.0 | 115 | 2.0 | 33.3 | 0.0 | 0.3 | 22.3 | 35.1 | 0.7 | 8.3 | 44.1 | 100.0 |
| 2 | 100.1 | 35.0 | 10.1 | 0.493 | 5.6 | 115 | 2.0 | 25.9 | 0.0 | 0.3 | 24.7 | 39.0 | 0.8 | 9.3 | 49.1 | 100.0 |
| 3 | 100.1 | 15.6 | 10.3 | 0.493 | 6.7 | 115 | 2.0 | 13.5 | 0.0 | 0.3 | 28.9 | 45.5 | 0.9 | 10.8 | 57.2 | 99.9 |
| 4 | 100.0 | 50.0 | 7.6 | 0.600 | 3.1 | 115 | 2.0 | 33.3 | 0.2 | 0.5 | 31.8 | 28.3 | 0.9 | 4.9 | 34.1 | 99.9 |
| 5 | 200.2 | 104.2 | 40.1 | 0.764 | 10.7 | 115 | 2.0 | 33.3 | 0.0 | 1.3 | 28.0 | 32.2 | 1.5 | 2.8 | 36.5 | 100.0 |
| 6 | 200.2 | 104.2 | 40.1 | 0.764 | 10.7 | 115 | 4.0 | 34.2 | 0.0 | 1.3 | 28.0 | 32.2 | 1.5 | 2.8 | 36.5 | 100.0 |
| 7 | 200.5 | 100.2 | 25.9 | 0.764 | 6.0 | 63 | 4.0 | 33.3 | 0.0 | 1.3 | 28.4 | 32.7 | 1.5 | 2.8 | 37.0 | 100.0 |
| 8 | 200.5 | 100.2 | 25.9 | 0.764 | 6.0 | 83 | 4.0 | 33.3 | 0.0 | 1.3 | 28.4 | 32.7 | 1.5 | 2.8 | 37.0 | 100.0 |
| 9 | 201.4 | 103.2 | 25.8 | 0.940 | 5.3 | 130 | 4.0 | 33.9 | 0.0 | 2.0 | 26.0 | 31.9 | 1.1 | 5.1 | 38.1 | 100.0 |
| 10 | 100.0 | 100.0 | 10.0 | 0.493 | 3.7 | 115 | 2.0 | 50.0 | 0.0 | 0.2 | 16.7 | 26.3 | 0.5 | 6.3 | 33.1 | 100.1 |
| 11 | 200.4 | 100.9 | 25.7 | 0.764 | 5.9 | 115 | 4.0 | 33.5 | 0.0 | 1.3 | 28.3 | 32.6 | 1.5 | 2.9 | 37.0 | 100.1 |
| 12 | 200.4 | 100.9 | 25.7 | 0.764 | 5.9 | 115 | 4.0 | 33.5 | 0.0 | 1.3 | 28.3 | 32.6 | 1.5 | 2.9 | 37.0 | 100.1 |
| 13 | 200.6 | 100.1 | 25.8 | 0.764 | 6.0 | 115 | 2.0 | 33.3 | 0.0 | 1.3 | 28.4 | 32.7 | 1.5 | 2.9 | 37.1 | 100.1 |
| 14 | 200.6 | 100.1 | 25.8 | 0.764 | 6.0 | 115 | 4.0 | 33.3 | 0.0 | 1.3 | 28.4 | 32.7 | 1.5 | 2.9 | 37.1 | 100.1 |

| Exp. No. | Bottoms (g.) | Phenol (g.) | Conc. Sulfuric Acid (g.) | Basicity of Bottoms meq/g | Free conc. Sulfuric acid (1) | Average Temp. (C.) | Time (hrs.) | Crude Product Composition (wt. %) (2) | | | | | | | | Reduction of Total Unknowns (%) | Remarks |
|---|---|---|---|---|---|---|---|---|---|---|---|---|---|---|---|---|---|
| | | | | | | | | Phenol | o-TAP | p-TAP | di-TAP | High-boilers | balance | Residue | Total Unknowns | | |
| 1 | 100.0 | 50.0 | 10.1 | 0.493 | 5.0 | 115 | 2.0 | 10.1 | 1.9 | 61.2 | 3.8 | 8.6 | 6.0 | 8.3 | 22.9 | 48.1 | (3) |
| 2 | 100.1 | 35.0 | 10.1 | 0.493 | 5.6 | 115 | 2.0 | 3.4 | 1.7 | 57.4 | 10.9 | 11.9 | 5.4 | 9.3 | 26.6 | 45.8 | (3) |
| 3 | 100.1 | 15.6 | 10.3 | 0.493 | 6.7 | 115 | 2.0 | 0.6 | 1.2 | 36.7 | 26.6 | 18.1 | 6.0 | 10.8 | 34.9 | 39.0 | (3) |
| 4 | 100.0 | 50.0 | 7.6 | 0.600 | 3.1 | 115 | 2.0 | 17.2 | 7.9 | 35.4 | 11.8 | 15.1 | 5.3 | 7.4 | 27.8 | 18.5 | |
| 5 | 200.2 | 104.2 | 40.1 | 0.764 | 10.7 | 115 | 2.0 | 14.5 | 1.6 | 49.2 | 2.2 | 12.7 | 7.5 | 12.3 | 32.5 | 11.0 | |
| 6 | 200.2 | 104.2 | 40.1 | 0.764 | 10.7 | 115 | 4.0 | 13.2 | 1.6 | 51.7 | 2.0 | 13.5 | 7.2 | 10.8 | 31.5 | 13.7 | |
| 7 | 200.5 | 100.2 | 25.9 | 0.764 | 6.0 | 63 | 4.0 | 17.9 | 7.2 | 23.9 | 11.8 | 24.0 | 2.1 | 13.1 | 39.2 | −5.9 | |
| 8 | 200.5 | 100.2 | 25.9 | 0.764 | 6.0 | 83 | 4.0 | 15.1 | 5.0 | 38.1 | 7.2 | 17.6 | 3.1 | 13.9 | 34.6 | 6.5 | |
| 9 | 201.4 | 103.2 | 25.8 | 0.940 | 5.3 | 130 | 4.0 | 13.5 | 2.1 | 50.4 | 3.8 | 15.0 | 5.1 | 10.1 | 30.2 | 20.7 | |
| 10 | 100.0 | 100.0 | 10.0 | 0.493 | 3.7 | 115 | 2.0 | 23.3 | 2.1 | 54.8 | 1.4 | 6.5 | 5.7 | 6.3 | 18.5 | 44.1 | (3) |
| 11 | 200.4 | 100.9 | 25.7 | 0.764 | 5.9 | 115 | 4.0 | 14.0 | 2.4 | 45.9 | 4.1 | 14.7 | 5.2 | 13.7 | 33.6 | 9.2 | (4) |
| 12 | 200.4 | 100.9 | 25.7 | 0.764 | 5.9 | 115 | 4.0 | 12.6 | 1.6 | 45.8 | 2.9 | 13.5 | 4.9 | 18.7 | 37.1 | −0.3 | (4) |
| 13 | 200.6 | 100.1 | 25.8 | 0.764 | 6.0 | 115 | 2.0 | 13.0 | 2.5 | 53.2 | 4.6 | 14.5 | 4.8 | 7.4 | 26.7 | | |
| 14 | 200.6 | 100.1 | 25.8 | 0.764 | 6.0 | 115 | 4.0 | 12.7 | 1.8 | 57.3 | 3.6 | 14.3 | 5.0 | 5.3 | 24.6 | | |

TABLE 1-continued

Examples 1 to 14

| | | | | | | | | |
|---|---|---|---|---|---|---|---|---|
| 13 | 200.6 | 100.1 | 25.8 | 0.764 | 6.0 | 115 | 2.0 | 28.0 |
| 14 | 200.6 | 100.1 | 25.8 | 0.764 | 6.0 | 115 | 4.0 | 33.7 |

(1) Free concentrated sulfuric acid (96.1%) per 100 g. of the reactants (bottoms + phenol).
(2) High-boilers refers to the unknowns appearing after the 2,4-di-TAP in the gas chromatogram. Balance refers to the unknowns appearing before the 2,4-di-TAP in the chromatogram. Residue refers to the non-GCeables present in the bottoms. Total unknowns is the sum of high-boilers, balance and residue. Wt. % of initial composition is based on the wt. of bottoms plus the phenol.
(3) Analysis carried out as GC area %. Recalculated as wt. % (the bottoms used in these Examples analyzed for approximately 12.5 wt. % non-GCeable residue). In all other experiments the analysis was carried out as GC wt. % using internal standard method.
(4) Concentrated sulfuric acid added before phenol. In all other experiments phenol was added before concentrated sulfuric acid.

Of the 14 examples shown in Table I, Example 1 illustrates the presently most preferred condition for the greatest reduction in the amount of total unknowns (48.1 % reduction) and is the process resulting in the greatest production of para-t-amylphenol (61.2%). The use of less phenol (Examples 2 and 3) with a slight increase in free acid gives less than the optimum result as shown in Table I. Lower levels of acid as in Example 4 when compared to Example 1 (otherwise same conditions) results in less of a reduction of the total unknowns (18.5% in Example 4), and produces only 35.4% para-t-amylphenol. Higher levels of acid as in Examples 5 and 6 also give less of a total reduction in unknowns. Example 7 shows that at a reaction temperature of 63° C. surprisingly gives an increase in the total unknowns. Comparing examples 11 and 12 with Examples 13 and 14 shows the importance of the mode of addition of the acid catalyst. Adding the sulfuric acid before the phenol (Examples 11 and 12) gives a lower reduction in total waste unknowns and a lower production of para t-amylphenol as compared to that found in Examples 13 and 14 where the sulfuric acid is added after the phenol.

The present invention may be embodied in other specific forms without departing from the spirit or essential attributed thereof and, accordingly, reference should be made to the appended claims, rather than to the foregoing specification, as indicating the scope of the invention.

We claim:

1. A process for reducing unknown constitutuents in waste distillation bottoms comprising a substantial proportion of unknown constituents, the waste distillation bottoms resulting from the production of a t-alkylphenol, and for substantially simultaneously producing a predominant amount of para-t-alkylphenol from the waste distillation bottoms comprising reacting with the waste distillation bottoms about 13 wt. % to about 50 wt. % phenol in the presence of about 3 wt. % to about 11 wt. % free acid catalyst available to catalyze the reaction, the acid catalyst being selected from the group consisting of Bronsted and Lewis acids, and maintaining an average reaction temperature of about 80° C. to about 130° C.

2. A process according to claim 1 wherein the waste distillation bottoms result from the production of a t-alkylphenol selected from the group consisting of para-t-alkylphenol, 2,4-di-t-alkylphenol and mixtures thereof.

3. A process according to claim 1 wherein the waste distillation bottoms include t-alkyl substituents of 4 to 12 carbons, whereby the para-t-alkylphenol produced contains t-alkyl substituents of 4 to 12 carbons.

4. A process according to claim 1 wherein the the acid catalyst is present in an amount of about 3.7 wt. % to about 7.0 wt. % free acid and the reaction temperature is maintained at an average of about 110° C. to about 120° C.

5. A process according to claim 4 wherein the phenol is present in an amount of 25 wt. % to about 34 wt. %, and the acid catalyst is present in an amount of about 5 wt. % to about 6 wt. %.

6. A process according to claim 5 wherein the average reaction temperature is maintained at about 115° C.

7. A process according to claim 6 wherein the reaction has a reaction time of about 2 hours to about 4 hours.

8. A process according to claim 1 wherein the reaction has a reaction time of about 2 hours to about 4 hours.

9. A process according to claim 1 wherein the acid catalyst is selected from the group consisting of concentrated sulfuric acid, hydrochloric acid, methanesulfonic acid, methanedisulfonic acid, acetonedisulfonic acid, p-toluenesulfonic acid, trifluoromethane sulfonic acid and boron trifluoride.

10. A process according to claim 2 wherein the acid catalyst is selected from the group consisting of concentrated sulfuric acid, hydrochloric acid, methanesulfonic acid, methanedisulfonic acid, acetonedisulfonic acid, p-toluenesulfonic acid, trifluoromethane sulfonic acid and boron trifluoride.

11. A process according to claim 2 wherein the para-t-alkylphenol is para-t-amylphenol.

12. A process according to claim 11 wherein the acid catalyst is concentrated sulfuric acid.

13. A process according to claim 12 wherein the phenol is present in an amount of about 25 wt. % to about 34 wt. %, and the concentrated sulfuric acid is present in an amount of about 5.0 wt. % to about 6.0 wt. % free acid, and the average reaction temperature is about 115° C.

14. A process according to claim 2 wherein the 2,4-di-t-alkylphenol is 2,4-di-t-amylphenol.

15. A process according to claim 1 wherein the phenol is added to and mixed with the waste distillation bottoms before the acid catalyst is added to and mixed with the waste distillation bottoms and phenol mixture.

16. A process according to claim 15 wherein the reaction takes place at a temperature of about 110° C. to about 120° C.

17. A process according to claim 16 wherein the reaction time is about 2 hours to about 4 hours.

* * * * *